US008872665B2

(12) United States Patent
Snodgrass

(10) Patent No.: US 8,872,665 B2
(45) Date of Patent: Oct. 28, 2014

(54) SANITIZATION COMPLIANCE MONITORING SYSTEM

(75) Inventor: David Snodgrass, Jupiter, FL (US)

(73) Assignee: Ultraclenz, LLC, Jupiter, FL (US)

( * ) Notice: Subject to any disclaimer, the term of this patent is extended or adjusted under 35 U.S.C. 154(b) by 0 days.

(21) Appl. No.: 13/612,095

(22) Filed: Sep. 12, 2012

(65) Prior Publication Data

US 2014/0070950 A1   Mar. 13, 2014

(51) Int. Cl.
| G08B 23/00 | (2006.01) |
| G08B 21/20 | (2006.01) |
| G08B 21/24 | (2006.01) |
| G08B 21/22 | (2006.01) |
| G06F 19/00 | (2011.01) |
| G08B 21/18 | (2006.01) |

(52) U.S. Cl.
CPC ............... *G08B 21/18* (2013.01); *G08B 21/20* (2013.01); *G08B 21/245* (2013.01); *G08B 21/22* (2013.01); *G06F 19/327* (2013.01)
USPC ..................................... 340/573.1

(58) Field of Classification Search
CPC ..... A61B 5/0002; A61B 5/002; A61B 5/0024; A61B 5/1115; G08B 23/00; G08B 21/20; G08B 21/22; Y10S 5/94
USPC ................. 340/573.1, 539.12, 572.1, 539.11, 340/13.24, 573.5; 235/375
See application file for complete search history.

(56) References Cited

U.S. PATENT DOCUMENTS

| 5,699,038 | A  | * | 12/1997 | Ulrich et al. ............. 340/286.07 |
| 6,774,800 | B2 | * | 8/2004  | Friedman et al. .......... 340/573.5 |
| 2010/0072271 | A1 | * | 3/2010 | Thorstensson ............... 235/375 |
| 2010/0117836 | A1 | * | 5/2010 | Seyed Momen et al. .. 340/573.1 |
| 2011/0309937 | A1 | * | 12/2011 | Bunza et al. ............... 340/573.5 |
| 2012/0119912 | A1 | * | 5/2012 | Ortega et al. ............... 340/573.5 |

\* cited by examiner

*Primary Examiner* — Phung Nguyen
(74) *Attorney, Agent, or Firm* — Lucas & Mercanti, LLP; Peter J. Phillips

(57) ABSTRACT

A sanitization compliance monitoring system comprises care giver badges, patient bed beacons associated with patient beds, dispenser beacons associated with sanitization dispensers, and a central unit for wirelessly communicating with the badges.

6 Claims, 14 Drawing Sheets

Welcome to UltraClenz

Please select your installation type.

Quick Links

Click for Dashboard

Click for System State

New Location

Start New Location Wizard

Existing Location

Add Device

Edit Device

View Data

FIGURE 6

Events

Dispense Events

Show 10 entries

| Device | Type | Nonce | FRID | FRT | FRQ | DT | ET |
|---|---|---|---|---|---|---|---|
| 300001E | Sanitizer | 121 | 9520009 | 09.56.00 11/01/2010 | 164 | 1 | 57655359 |
| 3E00019 | Sanitizer | 21 | 9520009 | 15.43.33 10/26/2010 | 107 | 1 | 57530611 |
| 3000019 | Sanitizer | 19 | 9520009 | 15.14.33 10/16/2010 | 93 | 1 | 57528873 |
| 3000019 | Sanitizer | 18 | 9520009 | 15.14.10 10/26/2010 | 133 | 1 | 57528615 |
| 3000D1E | Sanitizer | 28 | 9520009 | 13.49.45 10/23/2010 | 152 | 1 | 57523784 |
| 300001E | Sanitizer | 27 | 9520009 | 13.49.42 10/26/2010 | 173 | 1 | 57523782 |
| 300001E | Sanitizer | 20 | 9520009 | 08.12.25 10/28/2010 | 191 | 1 | 57503545 |
| 3000019 | Sanitizer | 10 | 9520009 | 07.44.40 10/26/2010 | 55 | 1 | 57501855 |
| 3000019 | Sanitizer | 8 | 9520009 | 07.15.51 10/26/2010 | 92 | 1 | 57500151 |
| 3000019 | Sanitizer | 7 | 9520009 | 07.15.49 10/26/2010 | 103 | 1 | 57500149 |

Showing 1 to 10 of 893 entries

Heartbeat Events

Show 10 entries

| Device | Type | Nonce | FRID | FRT | FRQ | DT | NHID | NHQA | GD | PS |
|---|---|---|---|---|---|---|---|---|---|---|
| 300001E | Sanitizer | 147 | 9520009 | 11.41.47 11/02/2010 | 166 | 1 | 9520009 | 208 | 1 | 0 |
| 3000019 | Sanitizer | 137 | 9520009 | 11.38.82 11/02/2010 | 114 | 1 | 9520009 | 122 | 1 | 0 |
| 3000031 | Sanitizer | 38 | 9520009 | 11.30.49 11/02/2010 | 127 | 1 | 9520009 | 160 | 1 | 0 |
| 3000028 | Sanitizer | 14 | 9520000 | 10.63.02 11/02/2010 | 191 | 1 | 9520009 | 200 | 1 | 0 |
| 300001E | Sanitizer | 145 | 9520009 | 10.41.47 11/02/2010 | 177 | 1 | 9520009 | 207 | 1 | 0 |
| 3000019 | Sanitizer | 136 | 9520009 | 10.38.02 11/02/2010 | 123 | 1 | 9520009 | 120 | 1 | 0 |
| 3000031 | Sanitizer | 37 | 9520009 | 10.30.49 11/02/2010 | 130 | 1 | 9520009 | 160 | 1 | 0 |
| 3000028 | Sanitizer | 13 | 9520009 | 09.53.02 11/02/2010 | 151 | 1 | 9520009 | 201 | 1 | 0 |
| 300001E | Sanitizer | 145 | 9520009 | 09.41.47 11/02/2010 | 190 | 1 | 9520009 | 207 | 1 | 0 |

FIGURE 7

| 3000019 | Sanitizer | 135 | 9520009 | 09.38.02 11/02/2010 | 107 | 1 | 9520009 | 120 | 1 | 0 |

Showing 1 to 10 of 15,543 entries

Generic Events

Show 10 entries

| Gateway | Device | Nonce | ET | Event Type | Battery Status | User ID (hex) |
|---|---|---|---|---|---|---|
| 9520009 | 2010002 | 75 | 13.42.21 01/01/2009 | 8 = Override Mode timeout | 92% | |
| 9520009 | 2010002 | 68 | 11.34.59 10/26/2010 | 4 = Unsanitary Room Exit | 92% | |
| 9520009 | 2010002 | 67 | 11.34.44 10/26/2010 | 2 = Unsanitary Room Entry | 92% | |
| 9520009 | 2010002 | 66 | 11.28.25 10/26/2010 | 2 = Unsanitary Room Entry | 92% | |
| 9520009 | 2010002 | 64 | 11.07.50 10/26/2010 | 4 = Unsanitary Room Exit | 92% | |
| 9520009 | 2010002 | 63 | 11.07.39 10/26/2010 | 4 = Unsanitary Room Exit | 92% | |
| 9520009 | 2010002 | 62 | 11.06.59 10/26/2010 | 2 = Unsanitary Room Entry | 92% | |
| 9520009 | 2010002 | 61 | 11.05.51 10/26/2010 | 4 = Unsanitary Room Exit | 92% | |
| 9520009 | 2010002 | 60 | 11.05.41 10/26/2010 | 2 = Unsanitary Room Entry | 92% | |
| 9520009 | 2010002 | 59 | 10.21.47 10/26/2010 | 4 = Unsanitary Room Exit | 92% | |

Showing 1 to 10 of 1,266 entries

Lost Events

FIGURE 7 (CONT'D)

Add Device to Gateway

Device Information

Device ID:
3000019

Device name:
TF Dispenser - wood

Facility Information

Select Facility:
UltraClenz - Engineering & Production

Gateway

Select Gateway:
09520009

Location Information

Wing:
north

Floor:
1st

Department:
administration

Room:
conference room

Extra Information

Unit Type
- o Manual Dispenser
- ⦿ Touch Free Dispenser
- o Door Sintenel w/ RFID
- o Door Sintenel Product Type:
Foam / Sanitizer Product Name:
generic foaming sanitizer Save

FIGURE 8

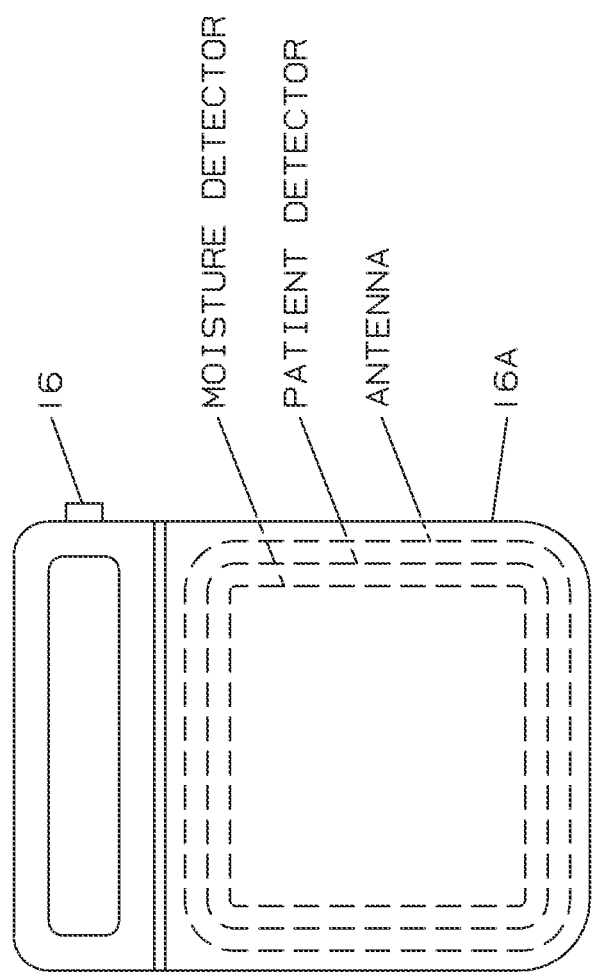

SANITIZATION COMPLIANCE MONITORING SYSTEM

BACKGROUND OF THE INVENTION

The present invention relates to a sanitization compliance monitoring system for a health care environment such as a hospital or nursing home, and particularly to a system to specifically target the hygienic state of a caregiver when interacting with a patient located in a patient bed.

Applicant's prior U.S. Ser. No. 61/437,466 filed Jan. 28, 2011, U.S. Ser. No. 61/486,491 filed May 16, 2011, and U.S. Ser. No. 13/215,823 filed Aug. 23, 2011, all of which are incorporated by reference in their entireties, relate to sanitization compliance monitoring systems.

The term "sanitization", as used herein, refers to using sanitizer, or performing a hand-wash procedure. The handwash procedure may be preferred using a sink and dispenser, including of the type disclosed in U.S. Pat. No. 6,426,701 to Levy, which is incorporated herein by reference. The handwash procedure monitored may be of the procedure disclosed in the Levy patent.

Sanitization compliance monitoring systems attempt to reduce or eliminate the number of occurrences of pathogens transferred from one patient to another via care givers in a health care environment. However, the systems do not fully monitor the sanitization state of the care giver based on his or her interaction with patients and sanitization procedures performed by the care giver.

As used herein, the terms, "care giver", "health care provider", and "user", are intended to be synonymous, and include any persons in a health care environment having the potential to spread pathogens, bacteria, etc., including not only doctors, nurses, orderlies and the like, but also custodians, maintenance and other personnel, and food personnel, etc., and any others who are in a health care facility, including other patients.

SUMMARY OF THE INVENTION in one form, the invention relates to monitoring whether a healthcare provider user has washed or sanitized his hands in a healthcare facility where the provider has exposure to different patients. The provider user would wear a badge which has three different colored lights to indicate cleanliness state of the hands of the wearer of the badge, red=contaminated (exposure to two or more different patients after a handwash), yellow=caution (exposure to only one patient after a handwash) and green=sanitized (exposure to no patients after a handwash). The yellow or caution state may indicate that the user should sanitize/wash within a certain time period.

Each patient bed would have an associated bed beacon which wirelessly communicates with a badge within a close range, to detect the identity of the badge, and to detect and change the badge's state (from green to yellow, or from yellow to red).

Each handwash or sanitizer station would have an associated handwash beacon to wirelessly communicate with a badge when in close proximity, to detect the badges identity, and to detect and change the badge state (from yellow or red, to green after a handwash procedure).

Whenever a user washes his hands at a handwash or sanitizer station, the handwash beacon would detect the badge identity and state, and the handwash beacon would cause the badge state to reset to green (from yellow or red).

If a user gets near a patient bed, the bed beacon would detect the badge identity and state, and the bed beacon would cause a green badge state to change to yellow, and if already in yellow because of earlier close proximity to a different patient bed beacon without an interim handwash, the bed beacon would cause the badge state to change from yellow to red.

The bed and dispenser beacons can communicate with a central monitoring unit which date stamps the communications received, and knows each of the badges' identities and when each badge changes from one state to another, to monitor the compliance of each badge wearer.

An audible alert may be triggered by the following:
  (1) a non-compliant event which triggers the audible alert to activate continuously at certain intervals until a compliance event occurs (wash, sanitize); and
  (2) when exiting a bed proximity boundary, the audible alert will activate one time reminding/warning the care giver that a compliant event needs to occur.

The objective of the badge wearer is to never reach a red=contaminated state. If a user is in a yellow state, indicating a single patient exposure, as soon as he leaves that patient he should wash and get his badge changed from yellow to green, and not come close to a different patient and reach red.

The dispenser beacon, which may be attached to a manual or touch-free dispenser, will set the care giver badge to the compliant state when activated. The dispenser beacon may be provided with functional status LEDs as follows:
  Green: one blink when speaking to a badge
  Red: two blinks means dead battery, one blink, low battery
  Red/Green: failed to communicate to the badge The dispenser beacon may be provided with a buzzer (Piezo), which is triggered by a successful transaction with the care giver.

The bed antenna of the bed beacon defines the proximity threshold/boundary of the care giver's badge around the bed, while the beacon communicates with the badge. The beacon will recognize when a care giver has entered or is within the proximity boundary, and trigger a patient contact event. It will then determine the badge's current compliant state. At this point, one of the following will occur:
  If the care giver badge is in the compliant (green) state, entering the proximity boundary will change the badge to a cautionary state (green-to-yellow).
  If the badge is in a cautionary (yellow) state, entering the proximity boundary will change the badge to a non-compliant red state. The beacon buzzer will activate (yellow-to-red).
  If the badge is already in a non-compliant (red) state, and the care giver enters the proximity boundary, the beacon buzzer will activate indicating a hyper-non-compliant state.

Every event will be recorded in a real-time basis. Each event will include the following data: time/date stamp; user's identification; beacon's identification; event type; battery status; badge; location of beacon; and location of dispenser.

All events recorded will be delivered to an off-site server. This data can be assessed by an Application Program Interface (API) raw data, or by web-based software (proprietary or non-proprietary).

The invention may include Hand Hygiene and Supply/Logistics Management Program.

The Supply/Logistics Management Program is a software system designed to assist users with the real-time analysis of hand hygiene practices and the overall management of dispenser usage throughout any facility. By inputting some basic installation information, a user will be able to know who is washing, where they are washing, and when they washed; know when a care giver is compliant, non-compliant, or about to be non-compliant; know when the batteries need to be replaced; know when a dispenser is not being used; be able to forecast chemical usage per dispenser, location, product, etc.; provide analytical reports of sales of the following: client name; city or state; facility location (floor, room, etc.); unit type; product type (lotion or foam); product name; and care giver (doctor, nurse, therapist, etc.).

The invention contemplates providing the user with an accessible website by which the user can set up the system and set up interface links.

Some advantages of the system may include:
Effective reminder system that can be used with and without badge (group vs. compliance monitoring);
Relatively easy and low-cost installation, battery-powered, cable-free connections;
Use of existing badge (retrofit), badges require minimal maintenance;
Self-sustained and independent network infrastructure;
Does not require the use of the installation facility's existing IT/Network;
Individual server not required;
Data analysis on and off the installed premises with remotely-accessible data;
Proprietary supply logistics software for analyzing and archiving data; and
Compliance monitoring using real-time data and/or multiple-bed monitoring.

The present invention may use one or more of the features disclosed in co-pending U.S. Ser. No. 12/150,223, filed Apr. 25, 2008; Ser No. 12/560,250, filed Sep. 15, 2009; Ser. No. 12/684,019, filed Jan. 7, 2010; and/or, Ser. No. 12/684,034, filed Jan. 7, 2010, all of which are incorporated herein by reference.

The present invention provides a sanitization compliance monitoring system for a health care environment having patient beds, comprising: badges wearable by persons, said badges having indicia representing a first-state indicating a sanitary compliant condition of the person, a second-state representing a cautionary state indicating the person's contact with a first patient, and a third-state representing an unsanitary state indicating the person's contact with a second patient after contact with, and different from, a first patient, said badges also having a wireless transmitter/receiver for communicating an identification signal unique to a single badge, and the current state of the badge; patient bed beacons, each associated with a different respective patient bed, each bed beacon having a transmitter/receiver capable of wirelessly communicating with said badges; dispenser beacons, each associated with a sanitization dispenser, and having a transmitter/receiver capable of wirelessly communicating with said badges; and wherein a badge in said first-state changes to said second-state when located in a certain proximity to a patient bed beacon, and transmits a status change signal indicating such first-to-second-state change to the patient bed beacon with the badge identification signal; wherein a badge in said second-state changes to said third-state when located in a certain proximity to a patient bed beacon different from the patient bed beacon which caused the badge to change from the first-state to the second-state, and transmits a status signal indicating such second-to-third-state change to the patient bed beacon with the badge identification signal, and wherein a dispenser beacon causes a badge to change from the second-state or third-state to the first-state when the person has performed a sanitization procedure at a sanitization dispenser beacon.

The system may further include a central unit for wirelessly communication with patient bed beacons, and wherein a patient bed beacon transmits the identification signal of the badge, and the current state of the badge, to the central unit, in response to the badge coming into a certain proximity with a patient bed beacon.

The system may further include a central unit for wirelessly communication with patient bed beacons, and wherein a dispenser beacon transmits the identification signal of the badge, and the current state of the badge, to the central unit, in response to the badge coming into proximity with a dispenser beacon.

The badges' indicia may comprise three different color lights respectively representing the first-, second-, and third-states. The badges may include an audio beeper in response to the dispenser beacon causing a change in the badge state from a second- or third-state to a first-state.

The system may provide, in response to a badge coming in close proximity to a dispenser beacon, that the badge transmitter/receiver and the dispenser transmitter/receiver increase their respective transmitter/receiver ranges to permit communication over a wider communication-range, and wherein the respective badge and dispenser beacon lock communication to the exclusion of other badges and dispenser beacons, until communication between the badge and dispenser beacon is complete.

The system may provide, in response to a badge coming in close proximity to a bed beacon, that the badge transmitter/receiver and the bed beacon transmitter/receiver increase their respective transmitter/receiver ranges to permit communication over a wider communication-range, and wherein the respective badge and bed beacon lock communication to the exclusion of other badges and bed beacons, until communication between the badge and bed beacon is complete.

The system may provide, that a badge in a second-state changes to the third-state if the badge leaves the certain proximity to a patient bed and remains out of that proximity for a certain time period and re-enters that certain proximity after the certain time period.

The system may provide, that a badge in the first-state changes to the second-state after a certain time period has elapsed without the badge-wearer performing a sanitization procedure.

The system may provide, that a badge in the second-state changes to the third-state after a certain time period has elapsed without the badge-wearer performing a sanitization procedure.

The present invention provides a method for monitoring sanitization compliance for a health care environment having patient beds, comprising: providing badges wearable by persons, said badges having indicia representing a first-state indicating a sanitary compliant condition of the person, a second-state representing a cautionary state indicating the person's contact with a first patient, and a third-state representing an unsanitary state indicating the person's contact with a second patient after contact with, and different from, a first patient, said badges also having a wireless transmitter/receiver for communicating an identification signal unique to a single badge, and the current state of the badge; providing patient bed beacons, each associated with a different respective patient bed, each bed beacon capable of wirelessly communicating with said badges; providing dispenser beacons, each associated with a sanitization dispenser, and having a transmitter/receiver capable of wirelessly communicating with said badges; changing the state of a badge from said first-state to said second-state when located in a certain proximity to a patient bed beacon, and transmitting a status change signal indicating such first-to-second-state change to the patient bed beacon with the badge identification signal;

changing the state of a badge from said second-state to said third-state when located in a certain proximity to a patient bed beacon different from the patient bed beacon which caused the badge to change from the first-state to the second-state, and transmitting a status signal indicating such second-to-third-state change to the patient bed beacon with the badge identification signal; changing the status of a badge from the second-state or third-state to the first-state when the person has performed a sanitization procedure at a sanitization dispenser.

The method may include wirelessly communicating with a central unit, and wherein a patient bed beacon transmits the identification signal of the badge, and the current state of the badge, to the central unit, in response to the badge coming within a certain proximity with a patient bed beacon.

The method may include wirelessly communicating with a central unit, and wherein a dispenser beacon transmits the identification signal of the badge, and the current state of the badge, to the central unit, in response to the badge coming within a certain proximity with a dispenser beacon.

The method may comprise illuminating badges' indicia with three different color lights respectively representing the first-, second-, and third-states.

The method may comprise generating an audio signal by a badge in response to the dispenser beacon causing a change in the badge state from a second- or third-state to a first-state.

The method may comprise, in response to a badge coming in a certain proximity to a dispenser beacon, that the badge transmitter/receiver and the dispenser transmitter/receiver increase their respective transmitter/receiver ranges to permit communication over a wider communication-range, and wherein the respective badge and dispenser beacon lock communication to the exclusion of other badges and dispenser beacons, until communication between the badge and dispenser beacon is complete.

The method may comprise, in response to a badge coming in close proximity to a bed beacon, that the badge transmitter/receiver and the bed beacon transmitter/receiver increase their respective transmitter/receiver ranges to permit communication over a wider communication-range, and wherein the respective badge and bed beacon lock communication to the exclusion of other badges and bed beacons, until communication between the badge and bed beacon is complete.

The method may comprise, that a badge in a second-state changes to the third-state if the badge leaves the certain proximity to a patient bed and remains out of that proximity for a certain time period and re-enters that certain proximity after the certain time period.

The method may comprise, that a badge in the first-state changes to the second-state after a certain time period has elapsed without the badge-wearer performing a sanitization procedure.

The method may comprise, wherein a badge in the second-state changes to the third-state after a certain time period has elapsed without the badge-wearer performing a sanitization procedure.

The present invention provides a hygiene system comprising a patient bed having a detector for detecting the presence of a patient within the bed; a bed beacon associated with a patient's bed in a health care facility, the bed beacon periodically transmitting a beacon signal during times when the patient's bed detector detects the presence of a patient within the bed; a user badge wearable by a healthcare worker which has at least two logic states, and which changes state from a first state indicating a hygiene compliance to a second state indicating patient exposure in response to the healthcare worker coming within a certain proximity of the bed beacon and detecting the beacon signal indicating the presence of a patient within the bed.

The detector may be a pressure sensor in the bed. The bed beacon may transmit a beacon signal using an antenna, which antenna changes a characteristic depending on whether a patient is detected within the bed. The characteristic may be parasitic capacitance of the antenna. The bed beacon may transmit a bed occupancy change signal whenever there is a change in occupancy of the bed. The system may further include a monitoring unit which receives bed occupancy change signals and time stamped data indicating the time of a change of occupancy of the bed.

The invention provides a hygiene dispenser system, comprising: a dispenser for dispensing hygiene product; a user badge wearable by a healthcare worker, said badge transmitting a signal; a beacon which detects the signal transmitted by the user badge; wherein the dispenser detects the presence of a user's hands, and produces an activation signal, and determines whether the beacon has detected a signal transmitted by a user badge and in response dispenses hygiene product, but wherein the dispenser will inhibit dispensing of hygiene product if the beacon has not detected a signal transmitted by a user badge.

The invention provides a hygiene system, comprising: a detector for detecting moisture in a patient bed in a healthcare facility due to a patient soiling the bed with waste matter, and for producing a bed soiled condition signal in response to said detection.

The system may include a bed beacon associated with the bed which transmits a bed soiled condition signal. The system may further include a monitoring station which receives bed soiling condition signals, and wherein the bed soiling condition signals identify the particular bed. The monitoring station may produce an alarm signal to notify healthcare personnel of the soiled condition. The monitoring station may store bed soiling condition events with a time stamp.

BRIEF DESCRIPTION OF THE DRAWINGS

FIG. 6 is a screenshot of a software program, with instructions for installing, modifying, or checking the status of the system;

FIG. 7 is a screenshot of monitoring data of dispense events of an installed system;

FIG. 8 is a screenshot of a display of menu items for setting or changing parameters of the system;

FIG. 10 is a view of a bed with a patient bed detector, and moisture detector.

DETAILED DESCRIPTION OF THE PREFERRED EMBODIMENT

Figure 1:
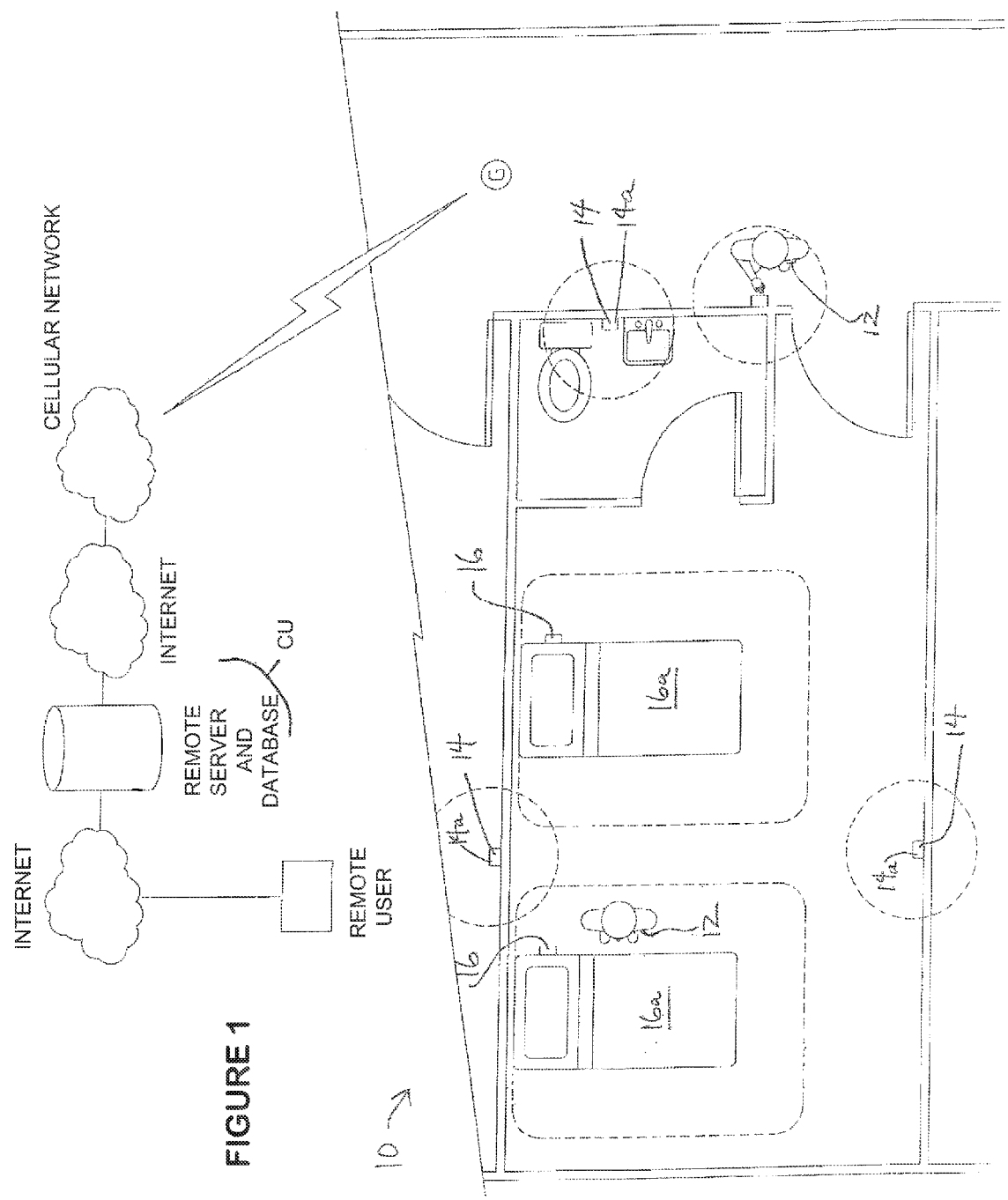
FIG. 1 is a block diagram of various components according to a preferred embodiment of the invention.

A detailed description of a preferred embodiment of the invention will be provided, but the invention is not limited to this embodiment.

The present invention provides a sanitization compliance monitoring system for a health care environment having patient beds, comprising: badges wearable by persons, said badges having indicia representing a first-state indicating a sanitary compliant condition of the person, a second-state representing a cautionary state indicating the person's contact with a first patient, and a third-state representing an unsanitary state indicating the person's contact with a second patient after contact with, and different from, a first patient, said badges also having a wireless transmitter/receiver for communicating an identification signal unique to a single badge, and the current state of the badge; patient bed beacons, each associated with a different respective patient bed, each bed beacon having a transmitter/receiver capable of wirelessly communicating with said badges; dispenser beacons, each associated with a sanitization dispenser, and having a transmitter/receiver capable of wirelessly communicating with said badges; and wherein a badge in said first-state changes to said second-state when located in a certain proximity to a patient bed beacon, and transmits a status change signal indicating such first-to-second-state change to the patient bed beacon with the badge identification signal; wherein a badge in said second-state changes to said third-state when located in a certain proximity to a patient bed beacon different from the patient bed beacon which caused the badge to change from the first-state to the second-state, and transmits a status signal indicating such second-to-third-state change to the patient bed beacon with the badge identification signal, and wherein a dispenser beacon causes a badge to change from the second-state or third-state to the first-state when the person has performed a sanitization procedure at a sanitization dispenser beacon.

The system may further include a central unit for wirelessly communication with patient bed beacons, and wherein a patient bed beacon transmits the identification signal of the badge, and the current state of the badge, to the central unit, in response to the badge coming into a certain proximity with a patient bed beacon.

The system may further include a central unit for wirelessly communication with patient bed beacons, and wherein a dispenser beacon transmits the identification signal of the badge, and the current state of the badge, to the central unit, in response to the badge coming into proximity with a dispenser beacon.

The badges' indicia may comprise three different color lights respectively representing the first-, second-, and third-states. The badges may include an audio beeper in response to the dispenser beacon causing a change in the badge state from a second- or third-state to a first-state.

The system may provide, in response to a badge coming in close proximity to a dispenser beacon, that the badge transmitter/receiver and the dispenser transmitter/receiver increase their respective transmitter/receiver ranges to permit communication over a wider communication-range, and wherein the respective badge and dispenser beacon lock communication to the exclusion of other badges and dispenser beacons, until communication between the badge and dispenser beacon is complete.

The system may provide, in response to a badge coming in close proximity to a bed beacon, that the badge transmitter/receiver and the bed beacon transmitter/receiver increase their respective transmitter/receiver ranges to permit communication over a wider communication-range, and wherein the respective badge and bed beacon lock communication to the exclusion of other badges and bed beacons, until communication between the badge and bed beacon is complete.

The system may provide, that a badge in a second-state changes to the third-state if the badge leaves the certain proximity to a patient bed and remains out of that proximity for a certain time period and re-enters that certain proximity after the certain time period.

The system may provide, that a badge in the first-state changes to the second-state after a certain time period has elapsed without the badge-wearer performing a sanitization procedure.

The system may provide, that a badge in the second-state changes to the third-state after a certain time period has elapsed without the badge-wearer performing a sanitization procedure.

The present invention provides a method for monitoring sanitization compliance for a health care environment having patient beds, comprising: providing badges wearable by persons, said badges having indicia representing a first-state indicating a sanitary compliant condition of the person, a second-state representing a cautionary state indicating the person's contact with a first patient, and a third-state representing an unsanitary state indicating the person's contact with a second patient after contact with, and different from, a first patient, said badges also having a wireless transmitter/receiver for communicating an identification signal unique to a single badge, and the current state of the badge; providing patient bed beacons, each associated with a different respective patient bed, each bed beacon capable of wirelessly communicating with said badges; providing dispenser beacons, each associated with a sanitization dispenser, and having a transmitter/receiver capable of wirelessly communicating with said badges; changing the state of a badge from said first-state to said second-state when located in a certain proximity to a patient bed beacon, and transmitting a status change signal indicating such first-to-second-state change to the patient bed beacon with the badge identification signal; changing the state of a badge from said second-state to said third-state when located in a certain proximity to a patient bed beacon different from the patient bed beacon which caused the badge to change from the first-state to the second-state, and transmitting a status signal indicating such second-to-third-state change to the patient bed beacon with the badge identification signal; changing the status of a badge from the second-state or third-state to the first-state when the person has performed a sanitization procedure at a sanitization dispenser.

The method may include wirelessly communicating with a central unit, and wherein a patient bed beacon transmits the identification signal of the badge, and the current state of the badge, to the central unit, in response to the badge coming within a certain proximity with a patient bed beacon.

The method may include wirelessly communicating with a central unit, and wherein a dispenser beacon transmits the identification signal of the badge, and the current state of the badge, to the central unit, in response to the badge coming within a certain proximity with a dispenser beacon.

The method may comprise illuminating badges' indicia with three different color lights respectively representing the first-, second-, and third-states.

The method may comprise generating an audio signal by a badge in response to the dispenser beacon causing a change in the badge state from a second- or third-state to a first-state.

The method may comprise, in response to a badge coming in a certain proximity to a dispenser beacon, that the badge transmitter/receiver and the dispenser transmitter/receiver increase their respective transmitter/receiver ranges to permit communication over a wider communication-range, and wherein the respective badge and dispenser beacon lock communication to the exclusion of other badges and dispenser beacons, until communication between the badge and dispenser beacon is complete.

The method may comprise, in response to a badge coming in close proximity to a bed beacon, that the badge transmitter/receiver and the bed beacon transmitter/receiver increase their respective transmitter/receiver ranges to permit communication over a wider communication-range, and wherein the respective badge and bed beacon lock communication to the exclusion of other badges and bed beacons, until communication between the badge and bed beacon is complete.

The method may comprise, that a badge in a second-state changes to the third-state if the badge leaves the certain proximity to a patient bed and remains out of that proximity for a certain time period and re-enters that certain proximity after the certain time period.

The method may comprise, that a badge in the first-state changes to the second-state after a certain time period has elapsed without the badge-wearer performing a sanitization procedure.

The method may comprise, wherein a badge in the second-state changes to the third-state after a certain time period has elapsed without the badge-wearer performing a sanitization procedure.

The present invention provides a hygiene system comprising a patient bed having a detector for detecting the presence of a patient within the bed; a bed beacon associated with a patient's bed in a health care facility, the bed beacon periodically transmitting a beacon signal during times when the patient's bed detector detects the presence of a patient within the bed; a user badge wearable by a healthcare worker which has at least two logic states, and which changes state from a first state indicating a hygiene compliance to a second state indicating patient exposure in response to the healthcare worker coming within a certain proximity of the bed beacon and detecting the beacon signal indicating the presence of a patient within the bed.

The detector may be a pressure sensor in the bed. The bed beacon may transmit a beacon signal using an antenna, which antenna changes a characteristic depending on whether a patient is detected within the bed. The characteristic may be parasitic capacitance of the antenna. The bed beacon may transmit a bed occupancy change signal whenever there is a change in occupancy of the bed. The system may further include a monitoring unit which receives bed occupancy change signals and time stamped data indicating the time of a change of occupancy of the bed.

The invention provides a hygiene dispenser system, comprising: a dispenser for dispensing hygiene product; a user badge wearable by a healthcare worker, said badge transmitting a signal; a beacon which detects the signal transmitted by the user badge; wherein the dispenser detects the presence of a user's hands, and produces an activation signal, and determines whether the beacon has detected a signal transmitted by a user badge and in response dispenses hygiene product, but wherein the dispenser will inhibit dispensing of hygiene product if the beacon has not detected a signal transmitted by a user badge.

The invention provides a hygiene system, comprising: a detector for detecting moisture in a patient bed in a healthcare facility due to a patient soiling the bed with waste matter, and for producing a bed soiled condition signal in response to said detection.

The system may include a bed beacon associated with the bed which transmits a bed soiled condition signal. The system may further include a monitoring station which receives bed soiling condition signals, and wherein the bed soiling condition signals identify the particular bed. The monitoring station may produce an alarm signal to notify healthcare personnel of the soiled condition. The monitoring station may store bed soiling condition events with a time stamp.

As shown in FIG. 1, the system 10 will consist of wireless care giver badges 12, wireless dispenser beacons 14 associated with sanitization dispensers 14a, and wireless patient bed beacons 16 associated with beds 16a. The badges 12 and beacons 14, 16, will communicate via embedded 125 kHz low frequency magnetic coupled (LFMC) radio transceivers. All devices will be battery powered. Event telemetry will be conveyed by the beacons to a central unit CU with an offsite event database via a separate 433 MHz wireless network (WiNET). The network transceivers will be embedded within the dispenser and patient bed beacons.

Figure 1A:
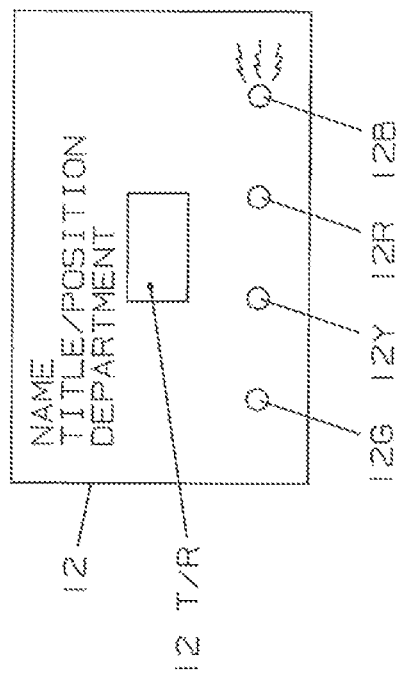
FIG. 1A shows a badge.

The care giver badge 12 will maintain and store the current hygienic state of its user. The user's hygienic state will be made visible to the user, and anyone able to see the user's badge 16, via LEDs located on the badges 12. There are three states supported by the badge 12, a first state of compliant (green LED), a second state of cautionary (yellow LED), and third state of noncompliant (red LED), FIG. 1A shows a badge 12 with green LED 12G, yellow LED 12Y, and red LED 12R.

The badge also has a place for the wearer's name and/or other indicia such as tide or position (doctor, nurse, orderly, etc.) and/or department (medical, maintenance, food service, etc.), which further identify the badge wearer to patients and other hospital personnel. Electronic data representing this information may also be transmitted between the badge, bed beacons and dispenser beacons. The badge 12 also has a beeper or acoustic transducer 12B, and a transmitter/receiver 12T/R, with appropriate electronics. The beeper 12B may transmit different sounds depending on the state of the badge, and the title or department, etc., as well as the number of recent or total times the wearer has experienced a "red" status. The different sound may be a difference in frequency, duration, warbling, etc. For wearers who frequently get a "red" status, for whom the sound may be distinctive, the patients or other persons will know that the wearer is a frequent violator and be extra cautious about contact with such wearer.

The bed beacon also has a transmitter/receiver 16T/R. The dispenser beacon also has a transmitter/receiver 14T/R. The badge, bed beacon and dispenser beacon have appropriate electronic circuitry, such as microprocessors or controllers, with memory and control programs, to perform the functions described herein.

The user's badge 12 is set to the compliant state when a sanitation event occurs. A sanitation event will occur when the user activates a dispenser 14a to dispense soap or sanitizer on their hands. The user's badge 12 is set to the noncompliant state when an unsanitary event occurs. An unsanitary event will occur when the user has contact with one patient and then has contact with a different patient without a sanitation event occurring in-between. The user's badge 12 is set to the cautionary state when they come in contact with a patient after having a prior sanitation event. This is not a noncompliant state, but, instead warns the user that a sanitary event needs to occur. If a sanitary event does not occur within 5 minutes, for example, after leaving a patient, the user's badge will set itself into the noncompliant state and thus generate an unsanitary event.

Figure 2:
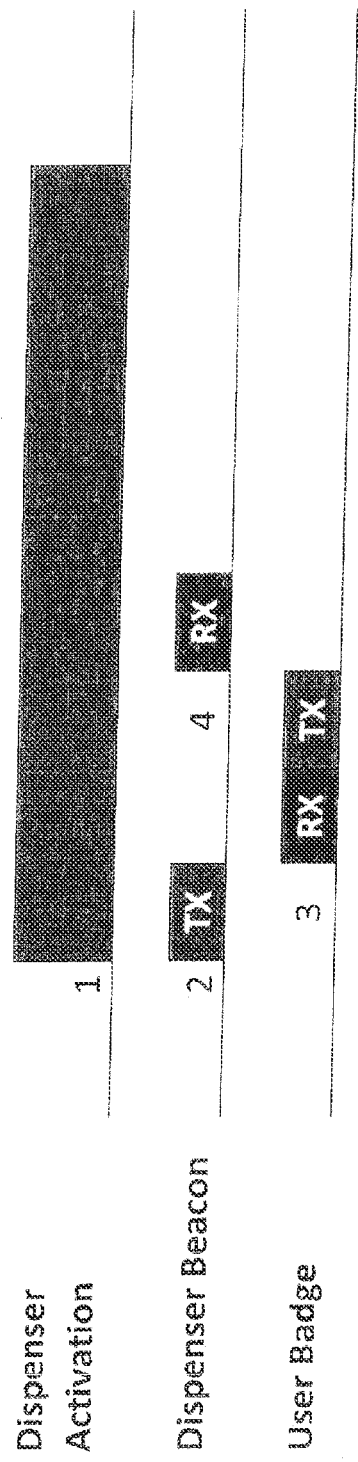
FIGS. 2 & 2A are timing diagrams showing communication between a dispenser and a user badge.

The dispenser beacon 14 is physically attached to a dispenser 14a via a cable that will provide the beacon with power, if the dispenser is battery-operated, and a signal indicating when the dispenser has been activated. As shown in FIG. 2, when a user activates the dispenser 14a, the beacon will detect the activation and send a polling message containing its unique ID and having an effective range, or proximity radius of 24" to 32", for example, (as shown by the dotted circles in FIG. 1). The user's badge, being within the aforementioned radius, will quickly reply by sending the dispenser beacon its identification number (ID) and current hygienic state. After the user's badge has sent its reply, it will set itself into the compliant state, store the unique ID of the dispenser beacon and create an audible beep to inform the user that the transaction is complete. When the dispenser activation is complete, the dispenser beacon will time and date stamp the sanitary event and send it along with the badge's ID and prior hygienic state to an offsite database via the WiNET wireless network.

Figure 3:
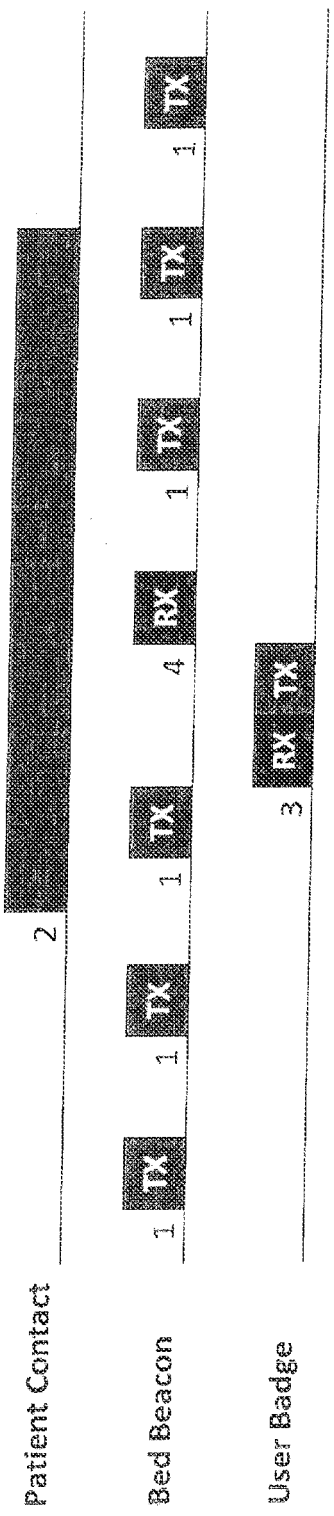
FIGS. 3 & 3A are timing diagrams showing communication between a bed beacon and a user badge.

The patient bed beacon will be physically attached to the patient bed and have an antenna that a) uses an insulated conductor to form a loop around the perimeter of the bed or b) uses a coil to inductively couple to the bed's metal frame without being in physical contact with the bed's metal frame. As shown in FIG. 3, the bed beacon will send a polling message containing its unique ID once every 1 to 5 seconds, for example. If a user's badge is within about 24" of the bed's perimeter (as shown by the dotted lines in FIG. 1), it will receive the polling message, store the bed beacon's ID and wait a random length of time to reply with its ID, hygienic state and the ID of the last dispenser used. Waiting a random length of time before replying to the bed beacon will reduce message collisions with any other badges approaching the bed at the same time. When the bed beacon 16 receives the user's badge ID, state and the ID of the last dispenser used, the transaction will be complete.

The bed beacon will continue to broadcast a polling message at regular intervals. The user's badge will receive the polling message and compare the received bed beacon's ID to the stored bed beacon ID. If they match, the user's badge will not reply. This will give other user's badges a chance to communicate and extend the badge's battery life.

Some hospitals require that care givers use dispensers inside the patient's room or in the hallway just outside of the patient's room before coming in contact with the patient. The bed beacon 16 can optionally be programmed with up to five, for example, dispenser IDs. These dispensers would be located within the patient's room or in the hallway just outside the patent's room. If programmed, and the user's badge is in a compliant state, the bed beacon will compare the programmed IDs with the ID of the dispenser last used by the badge wearer. If there is a match, the bed beacon 16 will instruct the user's badge to set itself to the cautionary state. Otherwise, the bed beacon 16 will instruct the badge to set itself to the noncompliant state. Programming the bed beacon 16 with the ID of the dispenser(s) in or near the patient's room, will require the badge wearer to use one of these dispensers for compliant patient contact. If the bed beacon is not programmed with dispenser IDs and the badge is in the compliant state, the bed beacon will instruct the user's badge to set itself to the cautionary state. This allows the badge wearer to use any dispenser for compliant patient contact. If the user's badge is in the cautionary state due to prior interaction with a different patient bed, the beacon will instruct the badge to set itself to the noncompliant state regardless of whether there are dispenser IDs programmed into the beacon or not.

When the transaction between the user's badge and the bed beacon is complete, the bed beacon will time and date stamp the patient contact event and send it along with the badge's ID, prior hygienic state and current hygienic state to the offsite database via the WiNET wireless network.

if other user badges are within range of the bed beacon, they will each wait for the next polling message from the beacon and reply after a random length of time. The first user badge to reply will transact with the bed beacon. All other user badges will wait for the next polling message after the current transaction is complete. This will continue until all user badges, within range of the bed beacon, have transacted.

A more detailed description of the operation of the above-described system follows, and will describe the general logic of how a dispenser, a care giver badge and a patient bed beacon will interact to provide a system of care giver hand hygiene compliance monitoring in a patient care setting such as a hospital, nursing home or similar facility. The system's logic will be illustrated using examples of successful and unsuccessful interactions.

Sanitary Care Giver and Single-Patient Interaction Example
1. The care giver activates a sanitization dispenser. The dispenser does not have to be in patient's room.
2. The dispenser will identify itself to the badge and the badge will set itself to the green state (sanitary state). An audible beep, from the badge, informs the care giver of the state change and the badge's green LED will blink about once per second. This event will be sent to the WiNET remote server via the dispenser beacon as a dispenser activation event with the dispenser and badge address, time and date. The badge will remain in the green state until a patient interaction occurs.
3. The care giver approaches a patient bed.
4. When within approximately 24" of the patient bed, the badge will detect the beacon associated with the bed.
5. The bed beacon will identify itself to the badge. The badge will tell the bed beacon that it is in the green state then set itself to the yellow state (cautionary state) to indicate patient contact. An audible beep, from the badge, informs the care giver of the state change and the badge's yellow LED will blink about once per second. This event will be sent to the WiNET remote server via the bed beacon as a sanitary/compliant patient interaction event along with the beacon and badge address, time and date.

The yellow state will inform the care giver, and anyone who sees the care giver's badge, that the care giver has been in recent contact with a patient and is in an unsanitary state. A timeout can be implemented that will set the badge to a red state (hygiene compliance violation state) if the badge remains in the yellow state too long (possibly 5 or 10 minutes, for example).

Unsanitary Care Giver and Single-Patient Interaction Example
1. Assume that the care giver's badge is currently in the yellow state (cautionary state) due to recent interaction with a patient.
2. The care giver approaches a patient bed.
3. When within approximately 24" of the patient bed, the badge will detect the bed's beacon.
4. The bed beacon will identify itself to the badge. The badge is in the yellow state, and the last interaction was with a different patient (bed beacon), so the badge will immediately set itself to the red state (hygiene compliance violation state). An audible beep from the badge, informs the care giver of the state change, and the badge's red LED will blink about onnce-per-second. The badge will also produce an audible alarm beep once-per-second, while in the red state. This event will be sent to the WiNET remote server via the bed beacon, as an unsanitary/noncompliant patient interaction event along with the bed beacon, and badge address, time and date.

5. The bed beacon will produce an audible alarm for a pre-determined period, 30 seconds, for example, after an unsanitary/non-compliant patient interaction occurs. The badge will remain in the red state until reset to the green state by activating a dispenser.

The red state will inform the care giver and anyone who sees or hears the care giver's badge, that the care giver has committed a hygiene compliance violation and needs to activate a dispenser immediately.

Unsanitary/non-compliant patient interaction events can be monitored in nearly real-time by other staff members via web based software connected to the WiNET offsite database. This allows for the execution of immediate corrective action.

Sanitary Care Giver and Multi-Patient Interaction Example

1. Assume that the care giver's badge is currently in the green state (sanitary state).
2. The care giver approaches patient one's bed.
3. When within approximately 24" of patient one's bed, the badge will detect the bed's beacon.
4. The bed beacon will identify itself to the badge. The badge will tell the bed beacon that it is in the green state then set itself to the yellow state (cautionary state). An audible beep from the badge informs the care giver of the state change, and the badge's yellow LED will blink about once-per-second. This event will be sent to the WiNET remote server via the bed beacon as a sanitary/compliant patient interaction event along with the bed beacon, and badge address, time and date.
5. When the care giver's interaction with patient one is complete, the care giver will leave the patient's bed side. The badge will remain in the yellow state.
6. The care giver approaches patient two's bed. Patient two could be in the same room with patient one or in a different room nearby.
7. When within approximately 24" of patient two's bed, the badge will detect the bed's beacon.
8. The bed beacon will identify itself to the badge. The badge is in the yellow state, and the last interaction was with a different patient (bed beacon), so the badge will immediately set itself to the red state (hygiene compliance violation state). An audible beep from the badge, informs the care giver of the state change, and the badge's red LED will blink about once-per-second. The badge will also produce an audible alarm beep once-per-second while in the red state. This event will be sent to the WiNET remote server via the bed beacon, as an unsanitary/noncompliant patient interaction event along with the beacon, and badge address, time and date.
9. When the care giver's interaction with patient two is complete, the care giver will leave the patient's bed side. The badge will remain in the red state until reset to the green state by activating a dispenser.
10. The care giver ignores the badge's red state, and approaches patient three's bed. Patient three could be in the same room with patient two, or in a different room nearby.
11. When within approximately 24" of the patient three's bed, the badge will detect the bed's beacon.
12. The bed beacon will identify itself to the badge. The badge is in the red state (hygiene compliance violation state), so the bed beacon will immediately sound its audible alarm, and the badge will remain in the red state. The badge's red LED will continue to blink about once-per-second. The badge will also continue to produce an audible alarm beep once per second while in the red state. This event will be sent to the WiNET remote server via the bed beacon as an unsanitary/noncompliant patient interaction event along with the beacon, and badge address, time and date.

The badge will store the address of the last bed beacon it interacted with. The bed beacon will broadcast its address at pre-determined intervals, (1 to 5 seconds for example). The badge will acknowledge the first broadcast it hears and store the address in temporary memory. Upon receiving subsequent bed beacon broadcast, the badge will compare the bed beacon's address to the one stored in memory. If the addresses match, the badge will ignore the broadcast. If the addresses don't match, the badge will know it is interacting with a different bed beacon, and will react based on its current state. If in the yellow state, go to the red state. If in the red state, it will stay in the red state.

Unsanitary/non-compliant patient interaction events can be monitored in nearly real-time by other staff members via web-based software connected to the WiNET offsite database. This allows for the execution of immediate corrective action.

Activating a dispenser will cause the badge to reset itself to the green state and clear the stored bed beacon's address. While in the green state, interaction with any bed beacon will cause the badge to go from the green state to the yellow state, and that bed beacon's address will be stored.

Figure 2A:
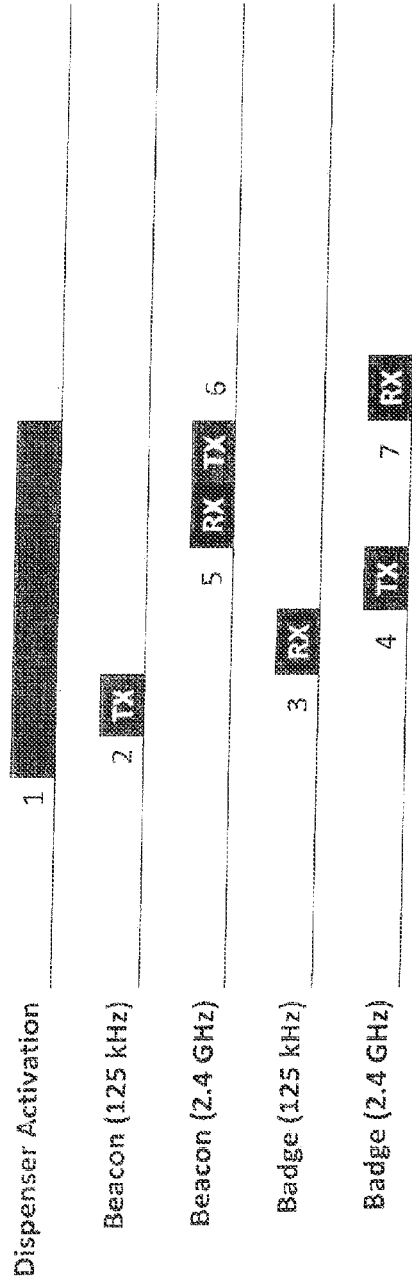
Figure 3A:
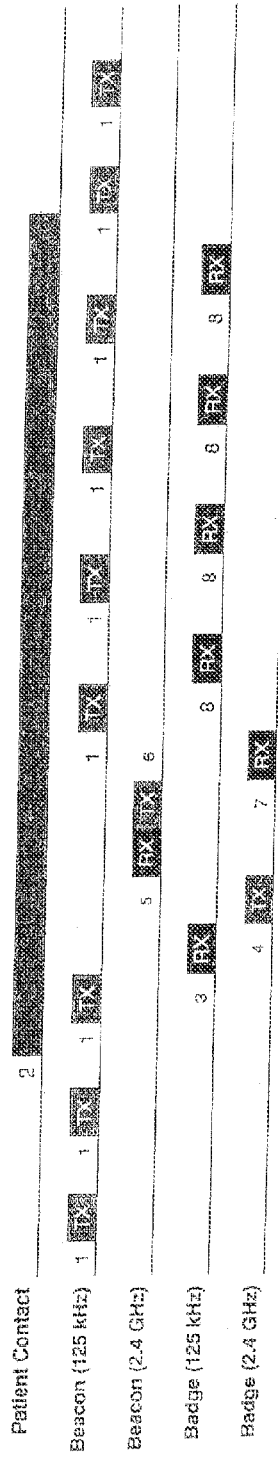
Figure 4:
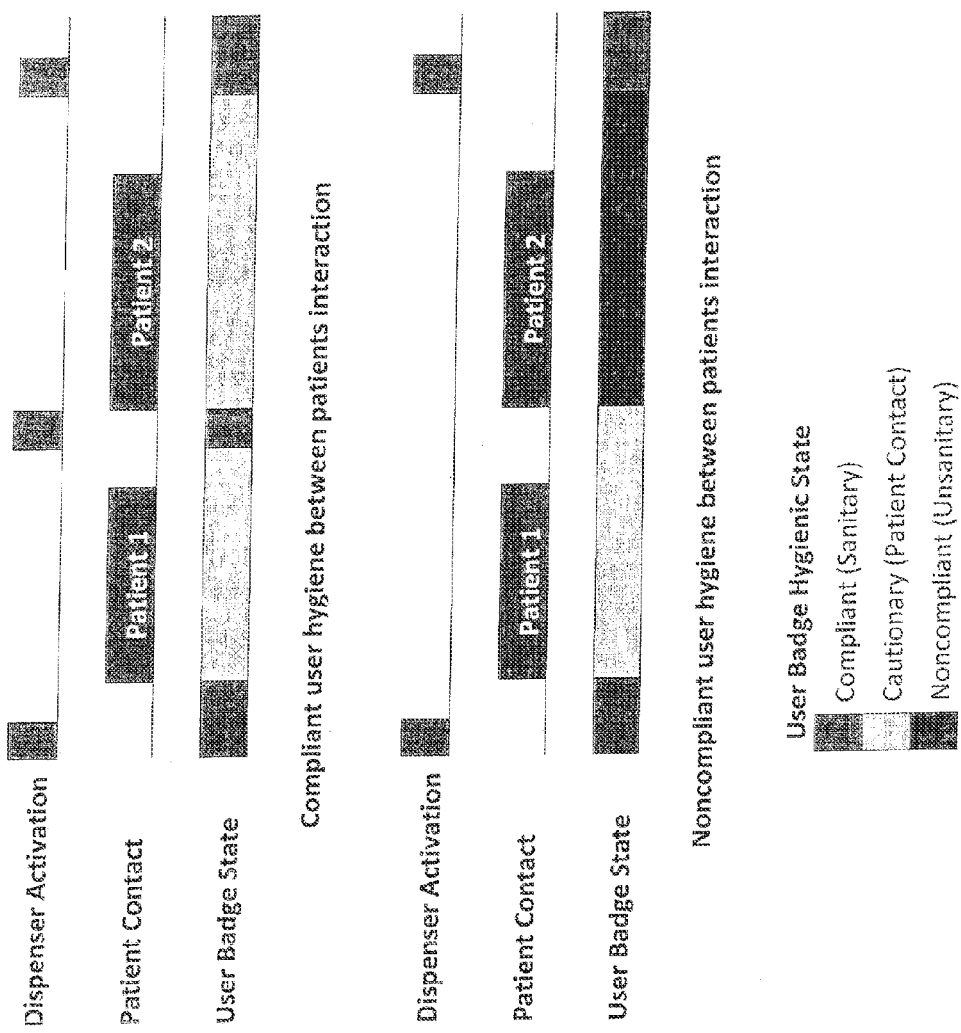
FIG. 4 is a diagram showing examples of user badge hygienic state and patient interaction.

The badge and beacons (both bed beacons and dispenser beacons) use a wireless medium to communicate with each other. As shown in FIGS. 2A and 3A, the wireless communications, between badges and beacons, may be separated into two distinct frequency ranges, low frequency (LF) and high frequency (HF).

The LF range is used primarily to "wake-up" the badge when it comes within close proximity of a beacon. The purpose of "waking-up" the badge is so that the micro controller (µC) (or CPU) can remain in a low power sleep state until needed. This will extend the life of the badge's battery. The badge is a mobile device that is worn by a user and therefore there is an advantage to having it as light weight and compact as possible. To this end, the battery powering the badge must be small. The current embodiment of the badge design may use a CR2032 3V lithium battery with a current capacity of only 200 mAh to 250 mAh.

The LF receiver may draw as little as between 2 µA and 6 µA and is able to detect a 125 kHz signal transmitted from a beacon. When a signal is detected, the receiver activates an input on the badge's µC which was preprogrammed to cause the µC to "wake-up" from a low power sleep state. Once awake, the µC then communicates with the receiver to read the beacon's address (or ID number) that is modulated on the 125 kHz signal.

A major advantage of using a LF signal is that its wavelength ($\lambda$) is very long. For 125 kHz, the wavelength is about 2,400 m. When the antenna's length (or circumference) is short relative to the signal's wavelength, the electromagnetic field radiated by the antenna is dominated by the magnetic field at close range. A magnetic field's power, as it propagates through space, will dissipate at a rate of $1/r^6$ where r=distance. A HF electromagnetic field such as RF will dissipate at a rate of $1/r^2$ and thus propagates farther through space with a much slower dissipation rate. Therefore, the rapid dissipation of a magnetic field makes it well suited for creating a distinct and predictable proximity boundary around a patient bed or dispenser that is similar to a wall. The boundary range can be adjusted by increasing or decreasing the current flowing through their respective LF loop antennae.

Once a badge has crossed within a patent bed's proximity boundary, it will detect the bed beacon's transmitted signal, wake-up and then read the bed beacon's address that is modulated on the signal. Now, the badge needs to send the beacon its address and current sanitary state. It would be possible for the badge to use LF to transmit this information but there are two reasons not to. First, a LF antenna needs to be designed to either transmit (series LCR tuned circuit) or receive (parallel LCR tuned circuit) to maximize efficiency. This would require two antennae for both the badge and the beacon which would add extra weight, size and cost to the badge. Second, the LF magnetic field has limited range. This is good for proximity detection but it isn't good for data communication. The badge's user may wander away from the patient bed's proximity boundary before the full exchange of data between the badge and beacon is complete, especially if the user is standing near the proximity boundary. The problem is even more likely when using a dispenser as the user will activate the dispenser and then immediately walk away.

To increase reliability of data communication beyond initial proximity detection, the badge will switch to hF to complete the transaction with a beacon. The HF signal has a much longer range allowing the badge to communicate with a beacon even if the user is 10 or 20 feet away from the beacon. The high frequency signal also has a short wavelength so a bidirectional antenna can be etch into the copper of the circuit board with no additional cost or weight added to the badge or beacons. In the current embodiment of the badge and beacon designs the HF signal is at a frequency of 2.4 GHz.

In addition or in lieu of the badge having three different colored LEDs to indicate the sanitary state of its wearer, the badge can receive the identity of the bed, and thus the patient ID or name of the patient presently occupying the bed. The badge can display the identity of the bed, the number of the patient, and/or the identity by name of the patient. The patient, upon seeing the badge, will be able to see this information on the badge and be assured that the user is sanitary for that patient. If the user's badge had a green state and entered the bed region for a certain patient, the badge could display the name of that patient, the identity of the bed and/or patient number. If the badge started out yellow (because of contact with a different patient area) or red, the badge would not change to the present patient's name. The present patient would thus not see their name on the user's badge, and could then alert the user to sanitize. Because the user would know that the patient has an easy way to detect whether the user has been sanitized for that patient, the user is more apt to comply with the sanitization protocols.

Figure 5:
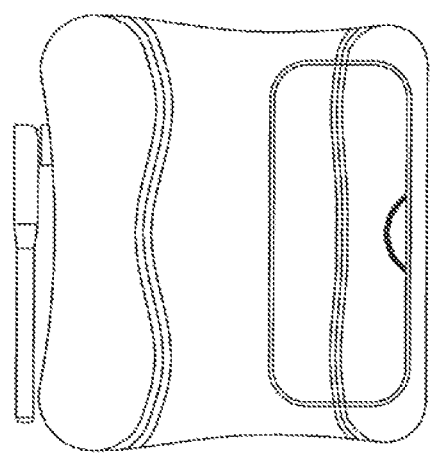
FIG. 5 is a view of a bed beacon.
Figure 9:
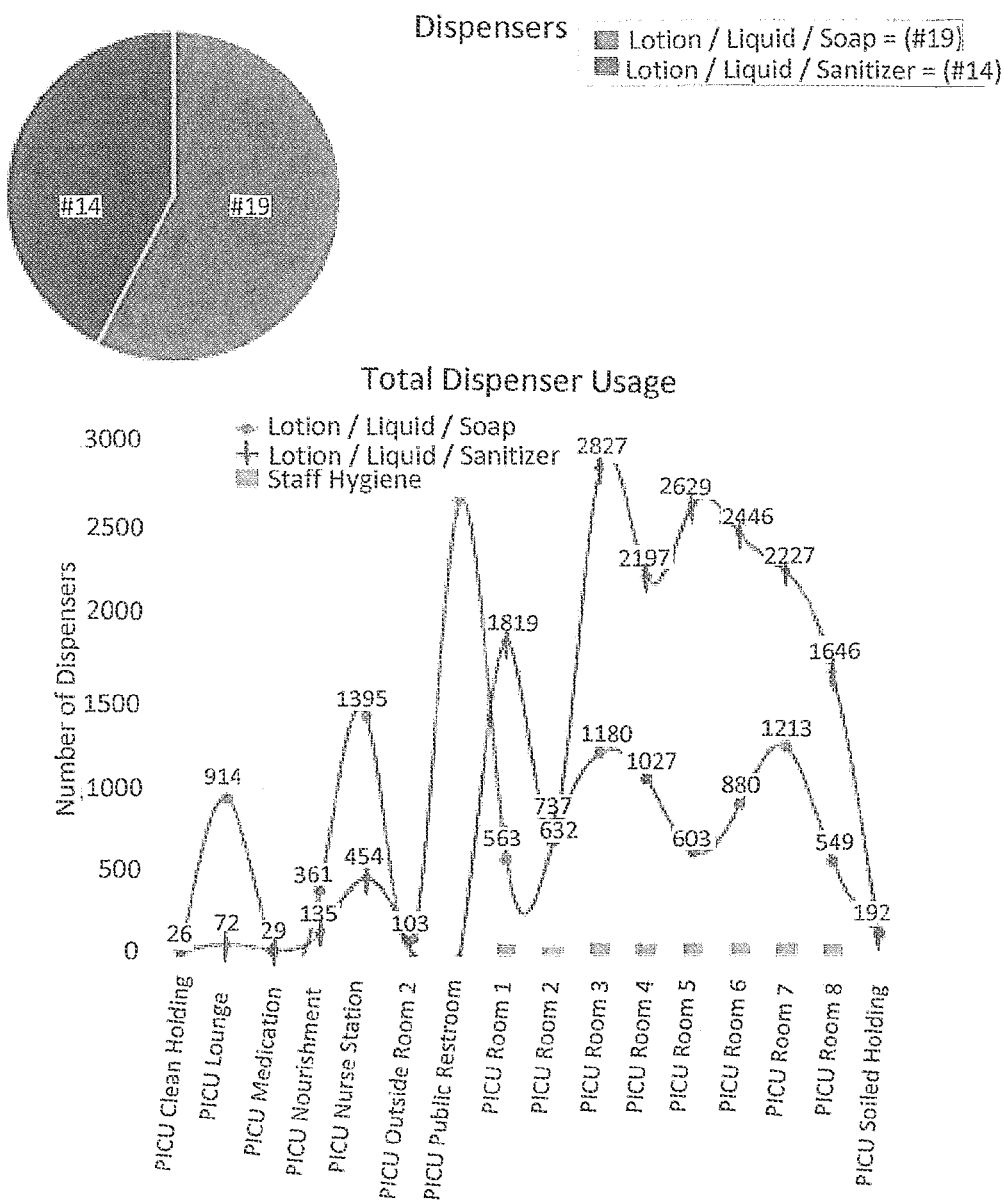
FIG. 9 is a display of the dashboard of the system, showing soap and sanitizer used at various dispenser locations.

FIG. 5 shows a view of a bed beacon, which has a body enclosing transmitter/receiver and appropriate electronics, as well as an antenna. The dispenser beacon may look the same, and may be larger or smaller.

The invention provides additional ways of minimizing risk of contamination of patients. If a caregiver wearing a badge is within the bed proximity but crosses over the proximity boundary and leaves the bed proximity zone for a certain period of time, for example, 5 seconds, an assumption is made that there is a reasonable likelihood that the caregiver has contacted a source of contamination (such as a bathroom or contaminated disposal area) which could pose a contamination risk to a patient within that bed proximity region. The badge state will then change from the basic yellow cautionary state to an elevated yellow cautionary state, still displaying yellow. In this elevated yellow cautionary state, if the caregiver returns to the same bed proximity region after that period of time (without sanitizing), the badge state will change to red, indicating a contamination risk to that patient in the bed.

If the caregiver wearing a badge leaves the bed proximity zone, but returns within the certain period of time (e.g., 5 seconds), it is assumed that the caregiver has not been exposed to a source of contamination, and the badge state does not change.

The mechanism to detect whether the caregiver has traveled and remained outside the bed proximity zone is the bed beacon which transmits a periodic bed beacon signal every second or so. The badge, if within the proximity zone, will receive the periodic bed beacon signal, and will transmit a signal back indicating that the badge is within the zone. However, when the badge travels outside the zone, the badge no longer receives the periodic bed beacon signal, and commences a time count. If, within the certain maximum safety time period (e.g., 5 seconds) the badge returns to within the bed proximity zone and again receives the periodic bed beacon signal, the time count is re-set to zero. But, if the time count reaches the certain maximum safety time period (e.g., 5 seconds), with the badge outside the bed proximity zone, the badge state changes to the elevated, yellow cautionary state. In the same manner as described above, in this elevated, yellow cautionary state, if the care giver returns to the same bed proximity region (without sanitizing), the badge state will change to red, indicating a contamination risk to that patient.

In another feature according to the invention, a badge will change state after the lapse of a certain inactivity time (a time within which a caregiver has neither been detected within a bed proximity zone, or has undergone sanitization). If the badge was in the green state, and a certain inactivity time of 60 minutes, for example, has elapsed, it is reasonable to assume that the caregiver has had some interaction with a source of contamination (such as a bathroom or contaminated disposal area), and the badge will change to yellow. If the badge is in the yellow state for whatever reason, and a certain inactivity time of 15 minutes, for example, has elapsed without sanitization (which would re-set the badge to green), the badge state will change to red.

The reason for the 60-minute inactivity time to trigger a green-to-yellow change, but the shorter inactivity time of 15 minutes to trigger a yellow-to-red change, is based on the assumption that a caregiver already in the yellow state poses more of a contamination-risk to bed patients (as well as other patients, caregivers and personnel, as well as other items or regions) when the caregiver's badge is already yellow, signifying that the caregiver has already had an exposure to a bed patient.

Of course, the 60-minute and 15-minute inactivity time periods can be changed, and can even be equal. The time periods can be selected based on the risk (perceived or actual) based on the environment, and even on a personal badge level, based on the particular caregiver, given his/her history of compliance and risk. Thus, different caregivers can have different time periods, depending on their history of compliance and risk.

The invention also provides a means of controlling or monitoring risk of contamination of a patient from a caregiver by monitoring whether a caregiver has one or more risk-control items, such as a respirator, mask, gown, gloves, or the like.

one example, any particular patient and/or patient bed region can be selectively defined to require caregivers coming in contact with the patient/bed to have one or more of these risk-control equipment items. The bed beacon associated with that patient can have means to selectively activate what risk-control items are required for that patient and/or patient bed region.

When a caregiver comes into the bed proximity zone, the bed beacon can detect whether the caregiver has the items required, by the items themselves having similar badges or other identification/communication devices associated with these items. For example, if the caregiver is required to wear, hut lacks a mask, the bed beacon will detect that the mask is missing because it failed to receive an acknowledgement signal for the mask when the caregiver entered the bed proximity zone. The bed beacon can then transmit a violation signal to the caregiver's badge (or separate badge), which will cause the badge to store and indicate a failure to comply, and the existence of a risk-situation. Tracking and detection of the risk-control items required by a caregiver can be done within the existing bed beacon and caregiver badges discussed above, or by different beacons and badges.

The invention may be used with equipment other than, or in addition to, beds, including any piece of equipment associated with patient care or use, such as wheelchairs, gurneys, recliners, intravenous unit, rehabilitation equipment, or diagnostic or treatment equipment, or the like.

Instead of, or in addition to, monitoring a patient bed or piece of equipment associated with a patient, the monitored equipment may be a place or region that poses a risk of contamination, such as a toilet, refuse container, urinal, bedpan, laundry (soil) area, medication room, or the like.

instead of detecting when a person comes into a contaminated area or region, one can detect when a person leaves a sanitary area or region, such as a handwash area, a sanitization area, food preparation, or service area, intensive care unit (IC), or newborn holding area.

The state of the badge can be a state indicating an (1) unsanitary state or condition; (2) a sanitary state; or (3) either an unsanitary or cautionary state.

The signal transmitted which indicates the state of the badge, includes transmitting which transition or change a badge is undergoing, e.g., red-to-green, green-to-yellow, etc.

The signal transmitted can indicate the state of the badge and badge identity, either by data within the signal, or by the manner in which the signal is transmitted, such as frequency, modulation technique, or signal conditioning.

The monitoring system of the invention can also be used to monitor when equipment, items, or parts of a room, have been sanitized. The badge can be attached to a sanitizer or disinfectant, such as a bleach product. The equipment, items, or parts of a room can be equipped with an associated beacon. The beacon can detect when the badge, and thus, sanitizer or disinfectant, are within a certain proximity and have thus sanitized or disinfected the area. The length of time that the badge is within the certain proximity can be detected and used to determine whether a proper sanitization or disinfecting has taken place according to a protocol or procedure. In a variation, the equipment, items, or parts, could be equipped with a badge, and the sanitizer or disinfectant could be engaged with a beacon. Even without badges, the system can detect when a dispenser device has dispensed products, thereby indicating when equipment, item, or part, or part of a room, has been sanitized.

The bed beacon system creates a barrier (patient zone) around the patient's bed via a modulated magnetic field. The magnetic field is generated by a 125 KHz modulated current flowing from the bed beacon through a coil type antenna as shown in FIG. 10. The antenna is connected to the bed beacon via a cable and it is currently mounted under the mattress of the patient bed. The magnetic field created by the antenna is detected by a health care worker (HCW) badge, worn by the HCW, when the HCW enters the patient zone. The badge will react to the magnetic field by changing its state based on the current hand hygiene state of the HCW.

The battery powered bed beacon continuously activates the magnetic field about once a second for a duration of less than 200 ms. This consumes a certain amount of current and the field is activated even if the patient is not in the patient bed. The bed beacon has a detector to detect the absence of the patient, so that it can stop activating the magnetic field when the patient is not in the patient bed. This adds significant life to the bed beacon batteries as well as prevents unnecessary hospital staff badge activation when a patient room or patient bed is unoccupied, i.e., when HCW hand hygiene is not necessarily required.

To facilitate detecting patient bed occupancy by the bed beacon, a pressure sensor as shown in FIG. 10 is added to the current magnetic field antenna design. As the antenna is a loop, there is space in the center of the antenna for pressure sensor placement. Therefore, the antenna and the pressure sensor could be manufactured as one unit. The cable connecting the antenna to the bed beacon would be expanded from 2 conductors to 4 conductors allowing both the antenna and the pressure sensor direct and independent connectivity to the bed beacon.

Another way to detect patient bed occupancy is to detect the change in parasitic capacitance seen by the bed beacon antenna. A patient lying above the antenna will create capacitance that will have a measurable detuning effect on the antenna. This detuning effect is used to determine when the patient bed is occupied without the need of a sensor or additional cabling.

Detecting patient bed occupancy has advantages beyond extending bed beacon battery life or preventing unnecessary HCW badge activations. The system can sound an alarm and/or notify HCW staff when a patient falls out of the patient bed or has left the patent bed without authorization or proper supervision. The system incorporates these features by utilizing the bed beacon with an occupancy detection equipped antenna to detect the moment when a bed becomes occupied or unoccupied and transmitting it as a time and date stamped event to the system network. This event could then be sent to a central monitoring station (and also to an offsite database) where software would analyze and then provide real-time status updates to web based software or provide real-time notifications to appropriate HCW personnel via text message, email or phone call.

Another feature that can be added to the patient bed is a moisture detector. This can be added with little or no additional cost as the antenna coils can be used for detection when laid out using the correct geometry. The benefit is that the bed beacon could detect when a patient soils their bed (urinates and/or defecates). The bed beacon will detect the moment when a bed becomes soiled and then transmit a time and date stamped event to the system network. This event would then be sent to a central station (and also to an offsite database) where software would analyze and then provide real-time status updates to web based software or provide real-time notifications to appropriate HCW personnel via text message, email or phone call. This will allow HCW personnel to turn over the patient's bed immediately with new bed sheets, and clean the patient with a bath and gown. This system feature would be especially valuable for notifying HCW personnel when a patient is unconscious or incapacitated and unable to notify HCW personnel themselves.

The system also provides an arrangement for inhibiting the dispensing of alcohol based hand sanitizers for non-HCW/staff persons. There have been cases when children and mentally compromised patients and/or visitors have dispensed alcohol based sanitizers for the purpose of consumption. There have also been cases when alcohol based sanitizers have been dispensed for use as an accelerant to start a fire. Both scenarios pose a serious risk to patient and facility safety.

The dispenser has a built-in electronic interface that is used to connect with a dispenser beacon. When the dispenser is activated, an output activation signal, in this interface, is activated so the beacon knows that the dispenser has been activated. This interface also has an input inhibit signal that when activated by the beacon will disable the dispenser's ability to dispense chemical.

The dispenser beacon can be programmed so that only a person wearing a PSS HCW Badge can activate the dispenser. The beacon will set the default state of the inhibit signal active. When a user places their hand under the dispenser, it will detect their hand and activate the activation signal. The beacon will detect the activation signal and then look for a HCW badge. If the user is wearing a badge, the beacon will detect it and then deactivate the inhibit signal. This will allow the dispenser to dispense chemical into the user's hand. If the user is not wearing a badge, the beacon will not detect a badge, keep the inhibit signal active and prevent the dispenser from dispensing chemical. Therefore, only a person wearing a PSS HCW badge will have the ability to dispense chemical from a touch-free dispenser equipped with a dispenser beacon.

Although one preferred embodiment has been described, the invention is not limited to this embodiment. Variations may be made within the scope of the invention, and the invention is defined only by way of the following claims.

What is claimed is:

1. A hygiene system comprising:
a patient bed having a detector for detecting the presence of a patient within the bed;
a bed beacon associated with a patient's bed in a health care facility, the bed beacon periodically transmitting a beacon signal during times when the patient's bed detector detects the presence of a patient within the bed using an antenna having a characteristic which changes depending on whether a patient is detected within the bed;
a user badge wearable by a healthcare worker which has at least two logic states, and which changes state from a first state indicating a hygiene compliance to a second state indicating patient exposure in response to the healthcare worker coming within a certain proximity of the bed beacon and detecting the beacon signal indicating the presence of a patient within the bed.

2. The system of claim 1, wherein the detector includes a pressure sensor in the bed.

3. The system of claim 1, wherein the characteristic is parasitic capacitance of the antenna.

4. The system of claim 1, wherein the bed beacon transmits a bed occupancy change signal whenever there is a change in occupancy of the bed.

5. The system of claim 4, further including a monitoring unit which receives bed occupancy change signals and time stamped data indicating the time of a change of occupancy of the bed.

6. A hygiene dispenser system, comprising:
a dispenser for dispensing hygiene product;
a user badge wearable by a healthcare worker, said badge transmitting a signal;
a beacon which detects the signal transmitted by the user badge;
wherein the dispenser detects the presence of a user's hands, and produces an activation signal, and determines whether the beacon has detected a signal transmitted by a user badge and in response dispenses hygiene product, but wherein the dispenser will inhibit dispensing of hygiene product if the beacon has not detected a signal transmitted by a user badge.

* * * * *